(12) United States Patent
Liu et al.

(10) Patent No.: US 10,428,139 B2
(45) Date of Patent: Oct. 1, 2019

(54) GM HYBRIDOMA CELL, MONOCLONAL ANTIBODY, KIT AND PREPARATION METHOD AND USE THEREOF

(71) Applicant: Dynamiker Biotechnology (Tianjin) Co., Ltd., Tianjin (CN)

(72) Inventors: Chunlong Liu, Tianjin (CN); Jie Peng, Tianjin (CN); Zhou Zhang, Tianjin (CN); Shuanzhu Zhai, Tianjin (CN); Ning Li, Tianjin (CN); Yan Su, Tianjin (CN); Zeqi Zhou, Tianjin (CN)

(73) Assignee: DYNAMIKER BIOTECHNOLOGY (TIANJIN) CO., LTD., Tianjin (CN)

( * ) Notice: Subject to any disclaimer, the term of this patent is extended or adjusted under 35 U.S.C. 154(b) by 0 days.

(21) Appl. No.: 16/172,175

(22) Filed: Oct. 26, 2018

(65) Prior Publication Data

US 2019/0062412 A1    Feb. 28, 2019

Related U.S. Application Data

(63) Continuation of application No. PCT/CN2017/090519, filed on Jun. 28, 2017.

(51) Int. Cl.
| | |
|---|---|
| *C07K 16/00* | (2006.01) |
| *C07K 16/14* | (2006.01) |
| *G01N 33/569* | (2006.01) |
| *C07K 16/44* | (2006.01) |

(52) U.S. Cl.
CPC .............. *C07K 16/14* (2013.01); *C07K 16/44* (2013.01); *G01N 33/56961* (2013.01); *C07K 2317/31* (2013.01); *C07K 2317/54* (2013.01); *C07K 2317/55* (2013.01); *C07K 2317/622* (2013.01); *C07K 2317/626* (2013.01); *G01N 2333/38* (2013.01)

(58) Field of Classification Search
CPC ...................................................... C07K 16/14
See application file for complete search history.

(56) References Cited

FOREIGN PATENT DOCUMENTS

| CN | 101149377 A | 3/2008 |
|---|---|---|
| WO | 2010082034 A | 7/2010 |

OTHER PUBLICATIONS

ISR of the international Searching Authority for PCT/CN2017/090519 dated Feb. 22, 2018.

*Primary Examiner* — Albert M Navarro
(74) *Attorney, Agent, or Firm* — Flener IP & Business Law; Zareefa B. Flener

(57) ABSTRACT

The present invention provides a hybridoma cell under the accession number CGMCC No. 13827. The hybridoma cell is capable of producing a monoclonal antibody against *Aspergillus* galactomannan antigen and a kit is prepared using the same. The kit provided by the present invention can specifically bind to the GM antigen, has both sensitivity and specificity of more than 95%, a detection limit of 0.85 ng/mL compared to 1 ng/mL of the existing product, and high compliance rate between the detection result and the reference reagent, and can provide more accurate and reliable detection results, so that IA can be detected early in the course of the disease and the patients can receive treatment in timely and effective manner, thereby improving the survival rate of patients. Moreover, the kit has simple and convenient operation, rapid and sensitive detection, which provides an effective tool for the quantitative detection of *Aspergillus* GM antigen.

17 Claims, 2 Drawing Sheets

GM HYBRIDOMA CELL, MONOCLONAL ANTIBODY, KIT AND PREPARATION METHOD AND USE THEREOF

CROSS-REFERENCE TO RELATED APPLICATION

This application is a continuation application of International patent application No. PCT/CN2017/090519, filed on Jun. 28, 2017, which is incorporated herein by reference in its entirety and for all purposes.

FIELD OF THE INVENTION

The present invention relates to the field of biotechnology, and in particular to a hybridoma cell producing a monoclonal antibody against *Aspergillus* Galactomannan (GM) antigen, a monoclonal antibody, a kit and a preparation method and use thereof.

BACKGROUND OF THE INVENTION

*Aspergillus* is a saprophytic bacterium that is widely found in nature and is a resident fungus of normal human skin mucosa. *Aspergillus* spores are small, have a diameter of 2-3 μm, can float in the air, and enter the human body through the respiratory tract. As the *Aspergillus* enters the body mainly through the respiratory tract, the *Aspergillus* infection mainly occurs in the lungs.

The incidence of invasive Aspergillosis (IA) in immuno-suppressed patients is increasing year by year due to the abuse of antibiotics and is the main cause of death. *Aspergillus fumigatus* is the most common pathogen causing severe deep *Aspergillus* infection in immunosuppressed patients, followed by *Aspergillus flavus, Aspergillus niger*, and *Aspergillus terreus*, etc. IA has a mortality rate as high as 70%-90% in patients with hematonosis and hematopoietic stem cell transplants (HSCT). The main reason for this high mortality rate is that IA cannot be effectively detected and diagnosed at the early stage of the course of disease, causing patients to die without timely and effective treatment. Therefore, it is of great significance to select early detection and diagnosis methods.

Currently, the widely recognized methods for detecting *Aspergillus* antigen mainly include 1,3-β-D glucan detection (G test) and galactomannan test (GM test). 1,3-β-D glucan antigen is a specific cell wall component of all fungi except the tubercle bacillus and *Cryptococcus*, with serum as a test sample, its sensitivity and specificity may reach 80%. However, because it is negative for colonized *Candida*, it often needs to be combined with the GM test for exclusion, when both are negative, fungal infection can be basically ruled out. In addition, the serological G test is susceptible to hematology and other factors such as fibrous substances, etc. Moreover, 1,3-β-D glucan antigen may form an immune complex with antibodies in the blood, which is rapidly cleared by the blood, resulting in a false negative.

Galactomannan is a highly specific and highly conserved polysaccharide present in cell wall of *Aspergillus*, which can be used as a specific molecular marker for detection of *Aspergillus*. Enzyme-linked immunosorbent assay (ELISA) is a relatively common method for detecting galactomannan. Acosta J reported that GM positive results were 4.3 days earlier than *Aspergillus* culture. A positive serum GM test is appropriate and applicable for the diagnosis of invasive fungal infections, and is further an important hint for patients taking early antifungal therapy, especially for some high-risk patients (such as HSCT patients). Therefore, determination of GM antigen levels in serum contributes to early diagnosis and early treatment of IA.

At present, the *Aspergillus* GM detection kits on the market have low sensitivity, specificity and sensitivity in detection, e.g., the sensitivity is about 83%, the specificity is 90%, and the detection limit is about 1 μg/L. They generally adopt a double antibody sandwich-enzyme linked immunosorbent assay, that is, first, a specific monoclonal antibody of *Aspergillus* is coated on an ELISA plate, and then a sample to be tested and the same monoclonal antibody labeled with horseradish peroxidase (HRP) are added, the antigen in the sample to be tested will bind to the specific monoclonal antibody and form a sandwich structure, then a color developing agent is further added for color development, and the depth of the color is positively correlated with the concentration of the antigen to be tested, thereby realizing the detection of GM antigen. The method has tedious detection steps, and high preparation cost of monoclonal antibody, which is not conducive to the promotion and popularization of the kits in clinical detection.

SUMMARY OF THE INVENTION

In one aspect, the present invention provides a hybridoma cell or a passage cell thereof capable of producing a monoclonal antibody against an *Aspergillus* galactomannan (GM) antigen. The hybridoma cell was deposited at the China General Microbiological Culture Collection Center (CGMCC) (address: No. 3, No. 1 Courtyard, Beichen West Road, Chaoyang District, Beijing, China, Institute of Microbiology, Chinese Academy of Sciences) on Apr. 18, 2017, with an accession number of CGMCC No. 13827.

The present invention also provides a monoclonal antibody or a specific antigen-binding fragment thereof, wherein the monoclonal antibody is produced by the above hybridoma cells. The monoclonal antibody or specific antigen-binding fragment thereof can specifically bind to *Aspergillus* GM antigen. Illustratively, the specific antigen-binding fragment includes (Fab')2, Fab, Fv, scFv, diabody, linear antibody or multispecific antibody and the like.

The present invention also provides a preparation method of the above monoclonal antibody, which includes preparation of ascites and purification of the monoclonal antibody, wherein the purification method includes saturated ammonium sulfate salting precipitation method and affinity chromatography.

The present invention further provides a detection reagent for detecting GM antigen and a detection method thereof, and the detection reagent comprises the above monoclonal antibody or specific antigen-binding fragment thereof. In the detection of GM antigen, a competitive ELISA method may be used, that is:

a) coating the GM antigen on a solid phase carrier;

b) treating a sample to be tested, then adding to the solid phase carrier with an enzyme-labeled anti-GM antigen monoclonal antibody, allowing the antigen in the sample to be tested to compete with the coated antigen for binding to limited antibody binding sites;

or, treating a sample to be tested, and adding to the solid phase carrier with an anti-GM antigen monoclonal antibody not labeled with an enzyme, allowing the antigen in the sample to be tested to compete with the coated antigen for binding to limited antibody binding sites, reacting at a constant temperature and thoroughly washing, adding an enzyme-labeled secondary antibody;

c) reacting at a constant temperature and thoroughly washing, and then adding a substrate solution of the enzyme to develop color, the depth of color is negatively correlated with the GM concentration in the sample to be tested; and d) measuring the absorbance (A value) at a certain wavelength with a microplate reader, and realizing the detection of the antigen by a standard curve.

The present invention also provides a detection kit and a preparation method thereof. The kit comprises the above monoclonal antibody or specific antigen-binding fragment thereof. The kit detects the *Aspergillus* GM antigen using a competitive ELISA method. Specifically, the kit comprises a GM antigen-coated solid phase carrier, an anti-GM antigen monoclonal antibody, and a GM antigen standard.

In a specific embodiment of the present invention, the solid phase carrier is an ELISA plate, a microwell plate, a test tube or a millipore filter; preferably, the solid phase carrier is an ELISA plate; and the material of the solid phase carrier may be, for example, polystyrene, nitrocellulose, nylon or the like.

In a specific embodiment of the present invention, the anti-GM antigen monoclonal antibody is an enzyme-labeled anti-GM antigen monoclonal antibody; preferably, the anti-GM antigen monoclonal antibody is an enzyme-labeled rabbit-derived anti-GM antigen monoclonal antibody.

Alternatively, the anti-GM antigen monoclonal antibody is an anti-GM antigen monoclonal antibody not labeled with an enzyme, and the kit further comprises an enzyme-labeled secondary antibody, and the enzyme-labeled secondary antibody can bind to the anti-GM antigen monoclonal antibody; preferably, the anti-GM antigen monoclonal antibody is a rabbit-derived anti-GM antigen monoclonal antibody not labeled with an enzyme, and the kit further comprises an enzyme-labeled goat anti-rabbit secondary antibody.

Wherein, the enzyme is Horseradish Peroxidase (HRP), Alkaline Phosphatase (AP) or Glucose Oxidase (GO); preferably, the enzyme is Horseradish Peroxidase.

In a specific embodiment of the present invention, the GM antigen standard comprises at least three GM antigen solutions with known concentrations. The GM antigen standard has a concentration in the range of 0-50 ng/mL; preferably, the GM antigen standard has a concentration in the range of 0-10 ng/mL, and most preferably in the range of 0-5 ng/mL.

In a specific embodiment of the present invention, the kit further comprises one or more of a sample treatment solution, a concentrated wash solution, a sample diluent, a substrate solution, and a stop solution.

Wherein, the sample treatment solution is selected from the group consisting of 0.03 mol/L EDTA, 0.1 mol/L EDTA, 0.12 mol/L EDTA, 0.05 mol/L proteinase K, 0.1 mol/L proteinase K, 0.2 mol/L proteinase K, 5% DMSO, 15% DMSO or 30% DMSO. Preferably, the sample treatment solution is 0.12 mol/L EDTA.

The preparation method of the kit includes:
1) preparing a GM antigen-coated solid phase carrier;
2) preparing a standard; and
3) preparing an anti-GM antigen monoclonal antibody.

Wherein, the step 1) further includes preparing a GM antigen coating solution, preparing a blocking solution and coating an ELISA plate.

The buffer of the GM antigen coating solution is selected from the group consisting of 0.1 mol/L Tris-HCl, 0.1 mol/L PBS, 0.05 mol/L CBS, 0.1 mol/L CBS, 0.2 mol/L CBS, and normal saline. Preferably, the buffer of the GM antigen coating solution is 0.1 mol/L Tris-HCl with a pH of 6.0-9.0;

The blocking solution is selected from the group consisting of 2% newborn calf serum, 5% newborn calf serum and 8% newborn calf serum. Preferably, the blocking solution is 8% newborn calf serum, which is prepared by adding newborn calf serum to normal saline.

The present invention also provides the use of a monoclonal antibody or a specific antigen-binding fragment thereof for the preparation of a detection reagent or a detection kit for detecting *Aspergillus* infection, and the monoclonal antibody is produced by the hybridoma cell under the accession number CGMCC No. 13827 or a passage thereof.

Illustratively, the specific antigen-binding fragment includes (Fab')2, Fab, Fv, scFv, diabody, linear antibody or multispecific antibody and the like.

The present invention has the beneficial effects that:

The hybridoma cell under the accession number of CGMCC No. 13827 or passage cell thereof provided by the present invention is capable of producing a monoclonal antibody which can specifically bind to the *Aspergillus* GM antigen and has high specificity. Moreover, a large amount of the monoclonal antibody can be obtained by culturing the hybridoma cell or passage cell thereof to solve the cost problem of preparing it into a kit for clinical promotion and popularization. Moreover, the detection kit provided by the present application can specifically bind to the GM antigen, has both sensitivity and specificity of more than 95%, a detection limit of 0.85 ng/mL compared to 1 ng/mL of the existing product, and high compliance rate between the test result and the reference reagent, and can provide more accurate and reliable test results, so that IA can be detected early in the course of the disease and the patients can receive treatment in a timely and effective manner, thereby improving the survival rate of patients, and further reducing the need for unnecessary empirical antifungal treatment. The kit provided by the present invention has simple and convenient operation, and rapid and sensitive detection. The microplate reader used is simple, popular, and inexpensive. The detection kit provides an effective tool for the quantitative detection of the *Aspergillus* GM antigen.

DETAILED DESCRIPTION OF THE INVENTION

Figure 1:
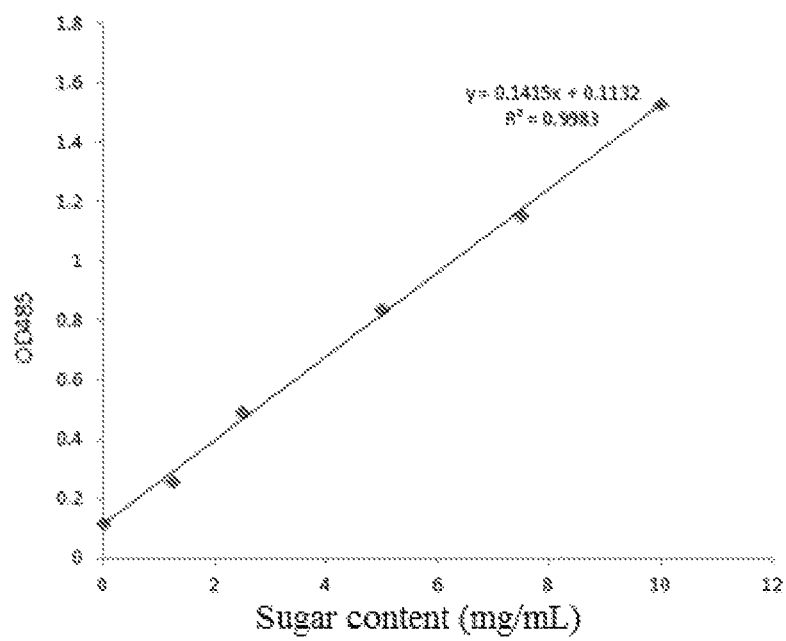
FIG. 1 shows a standard curve for determination of the polysaccharide content in the pure GM antigen of Example 1.

Example 1 Preparation of *Aspergillus* Galactomannan (GM) Antigen

The GM antigen was prepared using *Aspergillus*, and the *Aspergillus* strain used in the present invention was purchased from the American Type Culture Collection (ATCC) under the accession number ATCC 1022.

*Aspergillus* was cultured in a solid medium until the medium was covered with green spores. The hyphae were removed by filtration. The cells and spores were inactivated. After centrifugation, the spores were collected and washed, and crushed and filtered to remove spore fragments. The filtrate was subjected to alcohol precipitation and washing to obtain a crude GM antigen extract. The crude GM antigen extract was decolorized and ultrafiltered to obtain a GM antigen.

The solid medium is selected from the group consisting of PDA medium, Sabouraud medium or czapek's medium; preferably is PDA medium. Specific steps are as follows:

1. Preparation of Crude GM 2.0 L of PDA solid medium was prepared, the composition of which was 600 g of supernatant of boiled potato, 80.0 g of D-glucose, and 30.0 g of agar powder. *Aspergillus* strain was cultured in the medium at 25° C. for 3 days until the medium was covered with green spores. The spores were rinsed with sterile normal saline. The obtained spore suspension was filtered through 8 layers of sterile gauze 3 times to remove hyphae. Formaldehyde was added to the spore suspension to a final concentration of 3.7%, and the mixture was allowed to stand at 4° C. for 24 h to inactivate the cells and spores. The spores were collected by centrifugation at 12,000 g for 30 min at 4° C., and washed 6 times with sterile normal saline to remove formaldehyde which may be present. The spores frozen with liquid nitrogen were repeatedly ground. Then sterile normal saline was added thereto. Then the spores were broken with an ultrasonic cell disruptor. The resulting fluid containing the broken spores was filtered through a qualitative filter paper, and the filtrate was filtered through a 0.45 μm filter membrane to remove spore fragments. The resulting filtrate was transferred to a clean container, and 2.5 times by volume of absolute ethanol was added thereto. The mixture was allowed to stand at 4° C. overnight, and then centrifuged at 12,000 g for 30 min at 4° C. The resulting precipitate was dissolved in deionized water, and 2.5 times by volume of absolute ethanol was added thereto. The mixture was allowed to stand for 2 hours, and then centrifuged to separate the precipitate. The resulting precipitate was washed 3 times with absolute ethanol, and centrifuged at 12,000 g for 30 min at 4° C. The supernatant was discarded, and a crude GM was obtained.

2. Decolorization of Crude GM by Adsorption With Activated Carbon. The Specific Steps are as Follows GM was dissolved in 200 mL of deionized water. 3.0 g of activated carbon powder was slowly added thereto while stirring. The mixture was decolorized at 4° C. for 4 hours. After the claybank color of the solution was faded, it was filtered with a Buchner funnel repeatedly until the solution was clarified to obtain a GM extract from which the pigment was removed.

3. Purification of GM by Ultrafiltration. The Specific Steps are as Follows

The GM extract was suction filtered at room temperature to remove activated carbon particles. The resulting filtrate was filtered through a 0.22 μm filter membrane. The resulting filtrate was transferred to a 10 KD centrifugal ultrafiltration tube, and centrifuged at 4000 g for 20 min to obtain a high-purity GM.

4. Purification of GM, and Detection of Polysaccharide, Protein and Nucleic Acid Content of the Obtained GM Sample 1) The polysaccharide content of the pure GM antigen obtained above was determined by the Dubois-sulfuric acid phenol method. The detection results are shown in Table 1-1, Table 1-2, and FIG. 1:

TABLE 1-1

Polysaccharide content in pure GM antigen

| Sample name | Polysaccharide content (mg/mL) | OD485 |
|---|---|---|
| Standard | 0 | 0.118 |
|  | 1.25 | 0.257 |
|  | 2.5 | 0.495 |
|  | 5 | 0.837 |
|  | 7.5 | 1.155 |
|  | 10 | 1.532 |
| Detected sample | 2.203 | 0.425 |

TABLE 1-2

Polysaccharide content in pure GM antigen

|  | Volume (mL) | Polysaccharide content (mg) |
|---|---|---|
| Detected sample | 0.04 | 0.088 |
| All samples | 100 | 220 |

It can be seen from the detection results that 220 mg of pure *Aspergillus fumigatus* galactomannan antigen can be finally obtained from 2 L of *Aspergillus fumigatus* culture medium by the preparation method.

2) The pure GM antigen sample obtained by the preparation method was subjected to ultraviolet absorption detection. The samples were detected at the wavelength of UV 260 nm, UV 280 nm, and UV 320 nm, respectively. The results are shown in Table 2 below. As can be seen from the detection results, the total content of nucleic acids and proteins did not exceed 4% of the total mass of the sample.

TABLE 2

DNA and protein content in pure GM antigen

| Detection items | Concentration | Content (%) |
|---|---|---|
| DNA | 3.641 μg/mL | 0.16 |
| Protein | 74.583 μg/mL | 3.27 |
| Polysaccharide | 2.203 mg/mL | 96.57 |

5. Purification of GM, and HPLC Detection of the Obtained GM Sample

Figure 2:
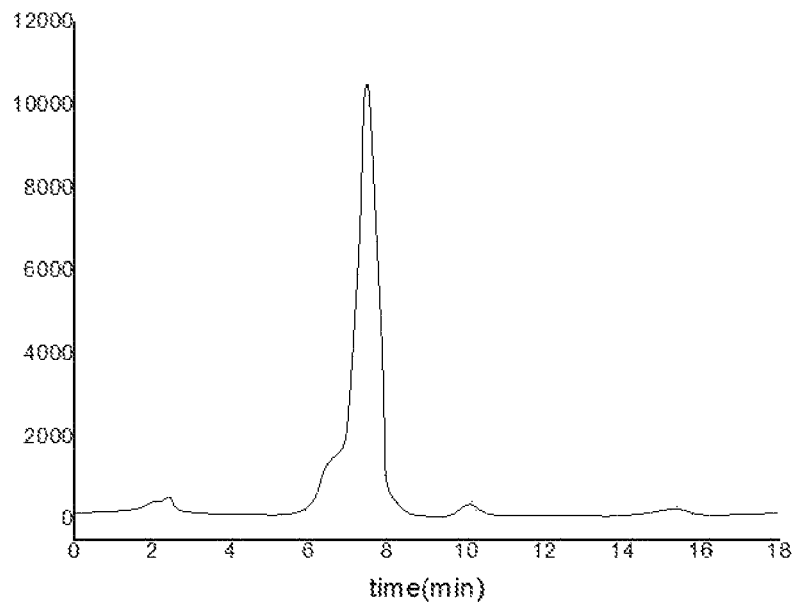
FIG. 2 shows the HPLC detection results of the pure GM antigen of Example 1.

The purified sample of the GM antigen obtained by the preparation method was subjected to HPLC detection. The detector was a refractive index detector. The detection results are shown in FIG. 2. As can be seen from FIG. 2, the sample showed a single peak with a narrow tip, and no obvious impurity peak appeared, indicating that the substance contained was uniform in size and high in purity.

6. Purification of GM Antigen by the Preparation Method, and Identification of the Antigen of the Obtained Pure GM Antigen Sample by *Aspergillus fumigatus* Antigen Detection Kit of Bio-Rad Laboratories At present, the GM antigen is generally detected by the *Aspergillus fumigatus* antigen detection kit of Bio-Rad Laboratories in the world. The GM antigen sample was detected with this kit at a sample concentration of 1 ng/mL. The detection results are shown in Table 3 below. As can be seen from the results, the GM antigen was positive and the OD value was greater than the positive control, indicating that the galactomannan antigen of *Aspergillus fumigatus* can be obtained by the method of the present invention.

TABLE 3

Detection results of antigen identification using
Bio-Rad *Aspergillus fumigatus* antigen detection kit

| Sample | OD450 | | | OD450 mean |
|---|---|---|---|---|
| Blank control | 0.045 | 0.046 | 0.046 | 0.046 |
| Negative quality control | 0.083 | 0.076 | 0.087 | 0.082 |
| Positive quality control | 0.972 | 0.951 | 0.936 | 0.953 |
| Cut off quality control | 0.408 | 0.389 | 0.419 | 0.405 |
| Detected sample | 1.352 | 1.408 | 1.315 | 1.358 |

Example 2 GM Antigen Modification

It is well known that the molecular size of a substance may affect its immunogenicity. The molecular weight of an effective immunogen is mostly above 10 kD. The larger the molecular weight, the stronger the immunogenicity. This may be because a macromolecular substance is easy to form a colloid in an aqueous solution, which stays in the body for a long time, has a great chance of contact with the immune cells, and is beneficial to stimulate the body to generate an immune response. In addition, the macromolecular substance has a relatively complex chemical structure, and thus has relatively many types and numbers of effective antigen genes.

The GM antigen obtained in Example 1 had a small molecular weight and poor immunogenicity, and needed to be coupled with a related macromolecular substance to enhance its immunogenicity. The macromolecule substance is one or more of latex microspheres, KLH (keyhole limpet hemocyanin), BSA (bovine serum albumin), and GST. A part of the coupling requires the addition of a crosslinking agent to promote the improvement of the crosslinking rate, and the obtained antigen polypeptide fragment can be used to immunize an animal.

In this example, the aminated latex microspheres were taken as an example. The specific coupling method is as follows:

1. 1 mL of microspheres (100 mg/mL) was washed twice with 10 mL of a washing/coupling buffer;
2. the microspheres were resuspended in 10 mL of glutaraldehyde solution (glutaraldehyde dissolved in the washing/coupling buffer at a concentration of 10%) to ensure sufficient suspension;
3. the mixture was reacted at room temperature (18-25° C.) for 1-2 h, and continuously stirred;
4. the microspheres were washed twice with the coupling buffer, and resuspended in 5 mL of the coupling buffer to ensure sufficient suspension;
5. an antigen was dissolved in 5 mL of the coupling buffer and mixed with the suspended microspheres;
6. the mixture was reacted at room temperature for 2-4 h, and continuously stirred;
7. the microspheres were washed, resuspended in 10 mL of a stop solution, gently stirred for 30 min, washed, resuspended in a storage buffer at a suitable concentration (usually 10 mg/mL); and
8. the microspheres were stored at 4° C. for use.

Example 3 Preparation of Anti-GM Antigen Monoclonal Antibody

Preparation of Anti-GM Antigen Monoclonal Antibody
1 Animal Immunity

Animals were immunized with GM antigen. Wherein, the immunization may be performed by subcutaneous injection, footpad injection, intrasplenic injection, intravenous injection or intraperitoneal injection, etc.; and the animals may be selected from rats, mice, guinea pigs, rabbits, chickens, sheep, horses, pigs or donkeys, etc. In this example, rabbits were used as animals for immunization. The specific steps are as follows:

The GM antigen and a Freund's complete adjuvant were mixed in an equal volume to a suitable volume, fully emulsified, and then injected into New Zealand white rabbits by subcutaneous multiple-point injection at an immunizing dose controlled at 0.01-0.1 mg per rabbit. Three days before immunization, ear blood was taken, and serum was separated as a negative control. The immunization was performed once every 2 weeks after the initial immunization, and the method was the same as the first time. The serum titer of the rabbit after immunization was measured.

2. Cell Fusion

An immune spleen cell refers to a B lymphoblast in an immune state in the spleen: plasmablast. Generally, the spleen 3 days after the last booster immunization is used to prepare a cell suspension. Since the proportion of B lymphocytes is large at this time, the success rate of cell fusion is relatively high.

First, the spleen was taken, and myeloma cells were activated. The myeloma cells were fused with spleen cells at a ratio of 1:10. The PEG fusion method was employed.

3. Screening and Cloning of Hybridoma Cells

After cell fusion, there are two parental cells and three randomly fused cells in the medium. In order to obtain hybridoma cells capable of secreting the target antibody, it is necessary to separate the successfully fused hybridoma cells from a large number of cells. Since B lymphocytes cannot survive in vitro for a long time, only myeloma cells and their own fused cells need to be removed. Therefore, it is necessary to culture the fused cells through a HAT medium to selectively retain the hybridoma cells.

On the 5th day after fusion, the growth of the cells could be observed. On the 10th to 14th day, the cell culture supernatant could be detected by indirect ELISA, and the positive hybridoma cells could be screened for cloning culture. The positive hybridoma cells were cloned and cultured by limiting dilution method. The positive hybridoma cells with the strongest titer of the detection results were expanded to a cell positive rate of 100%, and the cells were for further use. The titer of the culture supernatant of the hybridoma cells was measured by ELISA. The monoclonal hybridoma cells expanded in the culture were frozen in liquid nitrogen. The hybridoma cells were deposited with the China General Microbiological Culture Collection Center under the accession number of CGMCC No. 13827.

4. Preparation of Ascites

New Zealand white rabbits were injected intraperitoneally with 0.5 mL of paraffin oil. After 2 weeks, the hybridoma cells were collected and suspended in normal saline. 1 to $5 \times 10^6$ cells were suspended per 1 mL of normal saline. Then, each rabbit was intraperitoneally injected with 0.5 mL of the cell suspension and injected with a mixture of equal amounts of paraffin and Freund's incomplete adjuvant. After about 7-10 days, after the ascites was obviously produced, the rabbits were sacrificed, their abdominal cavities were cut open to suck and collect the ascites. The ascites was centrifuged at 12000 r/min for 15 min, added with an appropriate amount of a preservative, and stored at 4° C.

5. Purification of Monoclonal Antibody

Preliminary purification with saturated ammonium sulfate salting-out method:

2 mL of ascites sample was added with an equal volume of normal saline, followed by 4 mL of saturated ammonium sulfate solution, and the mixture was precipitated overnight at 4° C.;

the above mixture was centrifuged at 10000 g for 10 min at a low temperature, the supernatant was discarded, the precipitate was dissolved in 2 mL of PBS, and 1 mL of saturated ammonium sulfate solution was slowly added dropwise thereto, and the mixture was allowed to stand at 4° C. for 1 hour;

the above mixture was centrifuged at 10000 g for 10 min at a low temperature, the supernatant was discarded, the precipitate was dissolved in 1 mL of PBS and dialyzed with a PBS solution overnight at 4° C.

Further purification with affinity chromatography:

the column was washed with 5-10 bed volumes of elution buffer;

the column was washed with 5-10 bed volumes of coupling buffer;

the sample which was initially purified with saturated ammonium sulfate salting-out method was loaded;

the column was washed with 5-10 bed volumes of coupling buffer; and the column was eluted with 2-5 bed volumes of elution buffer to obtain an anti-GM antigen monoclonal antibody.

Wherein, the elution buffer is selected from the group consisting of 0.1 mol/L glycine buffer, PB buffer, citric acid-phosphate buffer, citric acid-sodium citrate buffer or acetic acid-sodium acetate buffer, pH 3.0; and the coupling buffer is selected from the group consisting of PBS buffer, Tris-HCl buffer, and acetic acid-sodium acetate buffer, preferably is PBS buffer.

Preparation of *Aspergillus* Galactomannan (GM) Antigen Immunoassay Kit

The specific preparation method is as follows:

I. Preparation of GM Antigen-Coated ELISA Plate

1. Preparation of GM Antigen Coating Solution

The GM antigen is diluted to 100 ng/mL-10 μg/mL with a buffer solution. The buffer solution is selected from the group consisting of: 0.1 mol/L Tris-HCl buffer with a pH of 6.0-9.0, 0.1 mol/L PBS buffer with a pH of 6.0-9.0, 0.05-0.2 mol/L CBS buffer with a pH of 6.0-9.0, or normal saline.

2. Preparation of Blocking Solution

2%-8% of newborn calf serum is added to a buffer solution to prepare a blocking solution. The buffer solution is selected from the group consisting of: 0.1 mol/L Tris-HCl buffer with a pH of 6.0-9.0, 0.1 mol/L PBS buffer with a pH of 6.0-9.0, 0.05-0.2 mol/L CBS buffer with a pH of 6.0-9.0, or normal saline.

3. ELISA Plate Coating

The prepared GM antigen coating solution is added into the well of an ELISA plate, 50-150 μL (preferably 100 μL) per well. The ELISA plate is coated at 12-18° C. (preferably 15° C.) for 6-8 h (preferably 7 h). The prepared blocking solution is added into the well of the ELISA plate, 50-150 μL (preferably 100 μL) per well, which is placed in an incubator at 12-18° C. (preferably 15° C.) for 2-4 h (preferably 3 h). The ELISA plate is taken out from the incubator. After discarding the blocking solution, the ELISA plate is incubated at a constant temperature of 20-25° C. (preferably 22° C.) for 2-4 h (preferably 3 h).

The ELISA plate may be modified prior to coating. The method includes placing the ELISA plate on a medical purification operation table equipped with an ultraviolet lamp, fixing the vertical distance between the ultraviolet lamp and the ELISA plate base, and selecting the different time periods to perform ultraviolet treatment on the ELISA plate.

II. Preparation of Standards (Establishment of Quantitative Standard Curve)

The standard is prepared by diluting GM antigen with 0.1 mol/L PBS. The concentrations of GM antigen are 5 ng/mL, 2.5 ng/mL, 1 ng/mL, 0.5 ng/mL, and 0.25 ng/mL, respectively.

III. Preparation of Anti-GM Antigen Monoclonal Antibody Solution

The anti-GM antigen monoclonal antibody solution is prepared by diluting the anti-GM antigen monoclonal antibody with an enzyme conjugate stabilizer at a ratio of 1:20000-1:40000 (preferably 1:30000).

The enzyme conjugate stabilizer is an agent capable of maintaining the stability between the antibody and the enzyme conjugate, and is capable of maintaining the activity of the antibody and the enzyme. Preferably, it may be an HRP enzyme conjugate stabilizer. The enzyme conjugate stabilizer in the present invention may be a commercially available product.

IV. Preparation of Enzyme-Labeled Secondary Antibody Solution

The enzyme-labeled secondary antibody solution is prepared by diluting a horseradish peroxidase (HRP)-labeled goat anti-rabbit secondary antibody with a HRP enzyme conjugate stabilizer at a ratio of 1:5000-1:20000 (preferably 1:10000).

V. Sample Treatment Solution

The sample treatment solution is a protein degeneration solution, preferably one or more selected from the following protein degeneration solutions: 0.05-0.2 mg/mL proteinase K, 0.03-0.18 mol/L EDTA (ethylene diamine tetraacetic acid) solution with a pH of 2-10, 5-30% DMSO (dimethyl sulfoxide) solution, and 1-8 mol/L urea with a pH of 7.0-8.0.

VI. Concentrated Wash Solution (20×0.01 M PBS)

The concentrated wash solution is a Tween-20-containing PBS solution (abbreviated as PBST solution), wherein the PBST solution may contain a biological liquid preservative such as ProClin300. In this example, the concentrated wash liquid was selected as follows:

in parts by weight, 160.0 parts of sodium chloride, 4.0 parts of potassium chloride, 31.6 parts of disodium hydrogen phosphate dodecahydrate, 2.8 parts of potassium dihydrogen phosphate, 0.2 part of Tween-20, 2 parts of ProClin300, and 1000 parts of ultrapure water, which were uniformly mixed.

VII. Sample Diluent

The sample diluent may be a CBS dilution containing 5-15% dried skim milk, BSA or bovine serum. In this example, a CBS dilution containing 10% dried skim milk was selected.

VIII. Substrate Solution

The substrate solution may be OPD (o-phenylenediamine), OT (o-toluidine), ABTS (2,2'-azino-bis(3-ethylbenzothiazole-6-sulfonic acid)) or p-NPP (p-nitrophenyl phosphate), preferably tetramethylbenzidine (3,3',5,5'-Tetramethylbenzidine, TMB).

IX. Stop Solution

The stop solution may be a 1-10 mol/L sulfuric acid solution, preferably a 2 mol/L sulfuric acid solution, which is prepared by diluting concentrated sulfuric acid with ultrapure water in a ratio of 1:8.

The present application tested various conditions in the above preparation methods. Wherein, in Examples 4-9, the effects of different GM antigen coating solutions on the detection repeatability of the kit were investigated; in Examples 10-11, the effects of different blocking solutions on the detection repeatability of the kit were investigated; and in Examples 12-18, the effects of different sample treatment solutions on the detection repeatability and recovery rate of the kit were investigated. The specific examples are shown in Table 4 below.

TABLE 4

Types and concentrations of coating solution, blocking solution and sample treatment solution in each of the examples

| Examples | Buffer in the coating solution | Final concentration of GM antigen | Blocking solution | Sample treatment solution |
|---|---|---|---|---|
| Example 4 | 0.1 mol/L Tris-HCl | 100 ng/mL | 2% newborn calf serum | 0.03 mol/L EDTA |
| Example 5 | 0.1 mol/L PBS | 100 ng/mL | 2% newborn calf serum | 0.03 mol/L EDTA |
| Example 6 | 0.05 mol/L CBS | 100 ng/mL | 2% newborn calf serum | 0.03 mol/L EDTA |
| Example 7 | 0.1 mol/L CBS | 100 ng/mL | 2% newborn calf serum | 0.03 mol/L EDTA |
| Example 8 | 0.2 mol/L CBS | 100 ng/mL | 2% newborn calf serum | 0.03 mol/L EDTA |
| Example 9 | Normal saline | 100 ng/mL | 2% newborn calf serum | 0.03 mol/L EDTA |
| Example 10 | 0.1 mol/L Tris-HCl | 5 µg/mL | 8% newborn calf serum | 0.1 mol/L EDTA |
| Example 11 | 0.1 mol/L Tris-HCl | 5 µg/mL | 5% newborn calf serum | 0.1 mol/L EDTA |
| Example 12 | 0.1 mol/L Tris-HCl | 10 µg/mL | 8% newborn calf serum | 0.12 mol/L EDTA |
| Example 13 | 0.1 mol/L Tris-HCl | 10 µg/mL | 8% newborn calf serum | 0.05 mol/L Proteinase K |
| Example 14 | 0.1 mol/L Tris-HCl | 10 µg/mL | 8% newborn calf serum | 0.1 mol/L Proteinase K |
| Example 15 | 0.1 mol/L Tris-HCl | 10 µg/mL | 8% newborn calf serum | 0.2 mol/L Proteinase K |
| Example 16 | 0.1 mol/L Tris-HCl | 10 µg/mL | 8% newborn calf serum | 5% DMSO |
| Example 17 | 0.1 mol/L Tris-HCl | 10 µg/mL | 8% newborn calf serum | 15% DMSO |
| Example 18 | 0.1 mol/L Tris-HCl | 10 µg/mL | 8% newborn calf serum | 30% DMSO |

Example 19 Preparation of Enzyme-Labeled Anti-GM Antigen Monoclonal Antibody Solution The horseradish peroxidase-labeled anti-GM antigen monoclonal antibody was diluted with a HRP enzyme conjugate stabilizer at a ratio of 1:20000.

Example 20 Detection Steps of *Aspergillus* Galactomannan Antigen Immunoassay Kit Two-Step Method:
a) a sample to be tested is mixed with a sample treatment solution in a volume ratio of 1:1 to 5:1 and boiled for 1-10 min, and then centrifuged to obtain a substance to be detected;
b) a GM antigen standard and the substance to be detected of step a) are separately mixed with an anti-GM antigen monoclonal antibody in an equal volume and incubated for 60 min-120 min;
c) the mixture of step b) is added to a GM antigen-coated ELISA plate and incubated for 60 min-120 min, and the plate is washed after incubation;
d) the ELISA plate of step c) is added with an enzyme-labeled secondary antibody and incubated for 20-60 min, and the plate is washed after incubation; and e) the ELISA plate of step d) is added with a substrate solution for color development for 10-15 min, and then added with a stop solution followed by determination, the absorbance value at 450 nm is read on a microplate reader, and the antigen is detected by a standard curve. The specific steps are as follows:

I. Treatment of Sample
1) a sample to be tested and a sample treatment solution are mixed at a volume ratio of 1:3 and then placed in a boiling water bath for 1 min;
2) the mixture after the water bath treatment is centrifuged at 1,000 g for 1 min; and
3) the supernatant after centrifugation is used for detection.

II. Detection Steps
1) a 96-well ELISA plate that has been pre-coated with an antigen is taken;
2) preparation of working wash solution: a concentrated wash solution is diluted 20 times (1 part of concentrated wash solution (20×0.01M PBS) is added with 19 parts of sterile deionized water or ultrapure water);
3) sample mixing: a standard curve group and a sample group to be tested are set, respectively, wherein,
  standard curve group: each standard curve point (the concentration of GM antigen standards are 5, 2.5, 1, 0.5, 0.25 ng/mL, respectively), and
  sample group to be tested: sample to be tested after treatment,
  the two groups of samples are separately mixed with a rabbit-derived anti-GM antigen monoclonal antibody in equal volumes, and the mixtures are separately transferred to the wells of an ELISA plate, 60 µL per well, and incubated at 37° C. for 60 min;

4) washing: the reaction solution was removed by swing, then each well is added with not less than 300 µL of wash solution each time, allowed to stand for 40 s and then patted dry, and the above washing operation is repeated 3 times;

5) addition of enzyme-labeled secondary antibody: after washing, each well is added with 60 µL of enzyme-labeled goat anti-rabbit secondary antibody, and incubated at 37° C. for 20 min;

6) washing: the same as step 4);

7) color development: after washing, each well is added with 60 µL of a substrate solution, and incubated at 37° C. for 15 min, protected from light;

8) stopping: each well is added with 50 µL of a stop solution, and uniformly mixed, the absorbance values are read at OD450 nm; and 9) calculation of results: the absorbance measurement values of the standard solution and the sample to be tested are respectively input in a computer, and the concentration values of the GM antigen in each sample to be tested are automatically calculated according to the semi-logarithmic standard curve and the equation drawn by a calculation software.

Alternatively, Detection Steps of *Aspergillus* Galactomannan Antigen Immunoassay Kit (One-Step Method)

a) a sample to be tested is mixed with a sample treatment solution in a volume ratio of 1:1 to 5:1 and boiled for 1-10 min, and then centrifuged to obtain a substance to be detected;

b) a GM antigen standard and the substance to be detected of step a) are separately mixed with an enzyme-labeled anti-GM antigen monoclonal antibody in an equal volume, and added to a GM antigen-coated ELISA plate and simultaneously incubated for 60-120 min, and the plates are washed after incubation; and c) the ELISA plate of step b) is added with a substrate solution for color development for 10-15 min, and then added with a stop solution followed by determination, the absorbance value at 450 nm is read on a microplate reader, and the antigen is detected by a standard curve. The specific steps are as follows:

1), and 2) are the same as 1) and 2) of the two-step method;

3) sample mixing: a standard curve group and a sample group to be tested are set, respectively, wherein, standard curve group: each standard curve point (the concentration of GM antigen standards are 5, 2.5, 1, 0.5, 0.25 ng/mL, respectively), sample group to be tested: sample to be tested after treatment, the two groups of samples are separately mixed with an enzyme-labeled anti-GM antigen monoclonal antibody in equal volumes, and the mixtures are separately transferred to the wells of an ELISA plate, 80 µL per well, and incubated at 37° C. for 90 min;

4) washing: the same as above;

5) color development: the same as above;

6) stopping: the same as above; and 7) calculation of results: the same as above.

Example 21 Clinical Application of *Aspergillus* Galactomannan Antigen Immunoassay Kit Using the kit of Example 10, the clinical application of the kit was tested in accordance with the two-step detection steps of Example 20.

1. Drawing of Standard Curve

Figure 3:
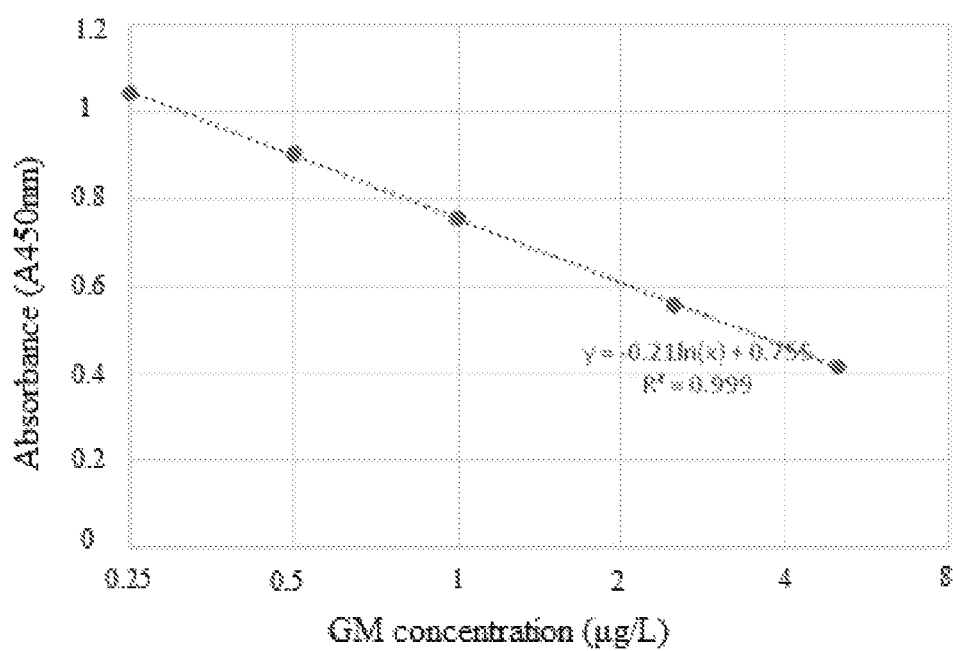
FIG. 3 shows a standard curve of the GM antigen immunoassay kit of Example 21.

Using the kit of Example 10, according to the detection steps of Example 20, the measured values of the respective standard curve points (5, 2.5, 1, 0.5, and 0.25 ng/mL) were obtained, as shown in Table 5. Using the data in Table 5, a standard curve, as shown in FIG. 3, was drawn with the logarithm value of the concentration of the GM antigen in the sample as the horizontal axis (x-axis) and the absorbance value measured at 450 nm as the vertical axis (y-axis), and a standard curve equation was obtained as: $y=-0.21 \ln(x)+0.755$, the linear correlation $R^2=0.999$, indicating that the standard curve equation fits well.

TABLE 5

Test standard curve

| Antigen concentration (ng/mL) | OD450 |
|---|---|
| 5 | 0.416 |
| 2.5 | 0.558 |
| 1 | 0.756 |
| 0.5 | 0.906 |
| 0.25 | 1.045 |

2. Determination of Reference Value of GM Antigen Immunoassay Kit

The samples, 30 positive samples clinically diagnosed as *Aspergillus* infection and 200 normal samples, were treated. The OD450 values were measured with the detection steps of Example 20 using the kit of Example 4. The GM antigen concentration values, as shown in Table 6, were calculated according to the standard curve (Table 5, FIG. 3).

TABLE 6

ELISA clinical detection results of reference value of GM antigen immunoassay kit

| Groups | Number of cases | GM concentration ($\bar{x} \pm s$ (ng/mL)) | Positive rate (%) |
|---|---|---|---|
| Normal sample | 200 | 0.45 ± 0.10 | 6.5 (13/200) |
| Positive sample | 30 | 1.55 ± 0.35 | 93.3* (28/30) |

Note:
*indicates P < 0.01 compared with normal sample.

The concentration of the detected GM antigen was calculated according to the results of the standard curve. By detecting 200 normal samples, the concentration value of the antigen in the 95% confidence interval was taken as the Cut-off lower limit: $\bar{x}$ (mean)+2 s (standard deviation)= 0.45+2*0.10=0.65, and by detecting 30 positive samples, the concentration value of the antigen in the 95% confidence interval was taken as the Cut-off upper limit: $\bar{x}$ (mean)−2 s (standard deviation)=1.55−2*0.35=0.85. A sample with an antigen concentration between 0.65 ng/mL and 0.85 ng/mL was suspected of infection. The obtained determination standard reference values of the GM antigen immunoassay kit are shown in Table 7.

TABLE 7

Determination standard reference value of GM antigen immunoassay kit

| Positive | Suspected | Negative |
|---|---|---|
| Antigen concentration ≥ 0.85 ng/mL | 0.65 ng/mL ≤ Antigen concentration ≤ 0.85 ng/mL | Antigen concentration ≤ 0.65 ng/mL |

If the detection result of the sample falls within the interval of Suspected, a secondary detection is required.

Example 22 Methodological Study of Kit

Using the kit of Example 10, the methodologies of the kit (sensitivity experiment, specificity experiment, recovery rate experiment, repeatability experiment, and stability test) were studied in accordance with the detection steps of Example 20.

1. Sensitivity Experiment 20 clinically diagnosed samples were collected for detection.

Diagnostic sensitivity=number of positive samples detected/total number of positive samples×100%. The experimental results are shown in Table 8. As can be seen from the results, the sensitivity of this experiment was above 95%.

TABLE 8

Sensitivity experiment results

| Serial number | OD450 | Calculated antigen concentration (μg/L) | Result determination |
|---|---|---|---|
| 1 | 0.695 | 1.33 | Positive |
| 2 | 0.570 | 2.4 | Positive |
| 3 | 0.625 | 1.85 | Positive |
| 4 | 0.493 | 3.45 | Positive |
| 5 | 0.720 | 1.18 | Positive |
| 6 | 0.593 | 2.15 | Positive |
| 7 | 0.502 | 3.31 | Positive |
| 8 | 0.637 | 1.75 | Positive |
| 9 | 0.576 | 2.33 | Positive |
| 10 | 0.708 | 1.25 | Positive |
| 11 | 0.819 | 0.74 | Suspected |
| 12 | 0.493 | 3.45 | Positive |
| 13 | 0.634 | 1.77 | Positive |
| 14 | 0.503 | 3.3 | Positive |
| 15 | 0.674 | 1.47 | Positive |
| 16 | 0.627 | 1.83 | Positive |
| 17 | 0.612 | 1.97 | Positive |
| 18 | 0.434 | 4.57 | Positive |
| 19 | 0.494 | 3.44 | Positive |
| 20 | 0.768 | 0.94 | Positive |

2. Specificity Experiment 20 healthy human samples were detected.

Specificity=number of negative samples detected/total number of negative samples×100%. The experimental results are shown in Table 9. As can be seen from the results, the specificity of this experiment was above 95%, and only one of the samples was detected as a suspected patient, which required a secondary detection.

TABLE 9

Specificity experiment results

| Serial number | OD450 | Calculated antigen concentration (μg/L) | Result determination |
|---|---|---|---|
| 1 | 0.915 | 0.47 | Negative |
| 2 | 0.971 | 0.36 | Negative |
| 3 | 0.919 | 0.46 | Negative |
| 4 | 0.849 | 0.64 | Negative |
| 5 | 0.910 | 0.48 | Negative |
| 6 | 0.989 | 0.33 | Negative |
| 7 | 0.996 | 0.32 | Negative |
| 8 | 0.893 | 0.52 | Negative |
| 9 | 0.938 | 0.42 | Negative |
| 10 | 1.040 | 0.26 | Negative |
| 11 | 0.902 | 0.5 | Negative |
| 12 | 0.977 | 0.35 | Negative |
| 13 | 0.989 | 0.33 | Negative |
| 14 | 0.802 | 0.8 | Suspected |
| 15 | 0.885 | 0.54 | Negative |
| 16 | 0.954 | 0.39 | Negative |
| 17 | 0.954 | 0.39 | Negative |
| 18 | 0.893 | 0.52 | Negative |
| 19 | 0.906 | 0.49 | Negative |
| 20 | 0.870 | 0.58 | Negative |

3. Recovery Rate Experiment

Normal human blood was added with *Aspergillus* galactomannan antigen to a concentration of 2 μg/L and 1 μg/L, and detected. The ratio of the true value to the expected value was calculated to obtain the recovery rate, as shown in Table 10. The recovery rate between 80-120% was considered acceptable. The experimental results showed that the recovery rate of this experiment was between 80% and 120%, indicating that the recovery rate is good. Moreover, when the concentration of the added antigen was 2 μg/L, the recovery rate was between 92% and 102%, which is closer to 100%.

TABLE 10

Recovery rate experiment results

| | OD450 | Calculated antigen concentration (μg/L) | Recovery rate |
|---|---|---|---|
| Concentration of the added antigen: 2 μg/L | 0.627 | 1.83 | 92% |
| | 0.621 | 1.89 | 95% |
| | 0.605 | 2.03 | 102% |
| | 0.622 | 1.88 | 94% |
| | 0.615 | 1.94 | 97% |
| | 0.624 | 1.86 | 93% |
| | 0.617 | 1.92 | 96% |
| Concentration of the added antigen: 1 μg/L | 0.780 | 0.89 | 89% |
| | 0.770 | 0.93 | 93% |
| | 0.747 | 1.04 | 104% |
| | 0.780 | 0.89 | 89% |
| | 0.766 | 0.95 | 95% |
| | 0.785 | 0.87 | 87% |
| | 0.764 | 0.96 | 96% |

4. Repeatability Experiment

1) Inter-Assay Precision

Criterion of acceptability: The same sample was tested once a day for 11 working days in the different batches of experiments, and its mean M, standard deviation SD and coefficient of variation CV were calculated. A kit with a coefficient of variation of CV≤25% was considered qualified. The results are shown in Table 11. Conclusion: The inter-assay precision (CV) of this product was 3%, which is far less than 25% and in line with the standard. It proves that the product has an excellent inter-assay precision, very small inter-assay dispersion degree and good repeatability.

TABLE 11

Inter-assay precision experiment results
Inter-assay precision summary

| Working day (d) | Calculated antigen concentration (μg/L) |
|---|---|
| 1 | 1.78 |
| 2 | 1.69 |
| 3 | 1.75 |
| 4 | 1.68 |

TABLE 11-continued

Inter-assay precision experiment results
Inter-assay precision summary

| Working day (d) | Calculated antigen concentration (µg/L) |
|---|---|
| 5 | 1.74 |
| 6 | 1.82 |
| 7 | 1.79 |
| 8 | 1.81 |
| 9 | 1.73 |
| 10 | 1.77 |
| 11 | 1.86 |
| M | 1.77 |
| SD | 0.0547 |
| CV | 3% |

2) Intra-Assay Precision

Criterion of acceptability: The same sample was tested in parallel for 10 sets of data in the same batch of experiments, and its mean M, standard deviation SD and coefficient of variation CV were calculated. A kit with a coefficient of variation of CV≤15% was considered qualified. The results are shown in Table 12. The product had an intra-assay precision (CV) of 1%, far less than 15%, which not only meets the standards, and passes the verification, but also shows that the intra-assay dispersion degree is very small and the repeatability is very good.

TABLE 12

Intra-assay precision experiment results

| Serial number | 1 | 2 | OD450 | Calculated antigen concentration (µg/L) |
|---|---|---|---|---|
| 1 | 0.634 | 0.638 | 0.636 | 1.76 |
| 2 | 0.637 | 0.635 | 0.636 | 1.76 |
| 3 | 0.632 | 0.641 | 0.637 | 1.75 |
| 4 | 0.641 | 0.633 | 0.637 | 1.75 |
| 5 | 0.633 | 0.638 | 0.636 | 1.76 |
| 6 | 0.635 | 0.632 | 0.634 | 1.78 |
| 7 | 0.637 | 0.643 | 0.640 | 1.72 |
| 8 | 0.635 | 0.636 | 0.636 | 1.76 |
| 9 | 0.631 | 0.633 | 0.632 | 1.79 |
| 10 | 0.642 | 0.634 | 0.638 | 1.74 |
| M | | | | 1.76 |
| SD | | | | 0.0184 |
| CV | | | | 1% |

5. Stability Experiment

The assembled kit was placed in an environment of 37° C., and used to prepare a standard curve and to detect an antigen solution with known concentration every day for 5 days. The rate of change of the detection value (CV) was less than 20%. The results are shown in Table 13, which proves that the kit is stable. The results showed that the coefficient of variation CV of 5 days was 3.5%, which is much less than 20%, indicating that the kit provided by the present invention has very good stability and makes the detection result more reliable.

TABLE 13

Stability experiment results

| | | 1 | 2 | 3 | 4 | 5 | CV |
|---|---|---|---|---|---|---|---|
| | Blank control | 0.047 | 0.051 | 0.058 | 0.048 | 0.055 | |
| Antigen concentration in standard curve (µg/L) | 0.25 | 1.078 | 1.083 | 1.036 | 1.089 | 1.046 | |
| | 0.5 | 0.917 | 0.925 | 0.911 | 0.945 | 0.916 | |
| | 1 | 0.764 | 0.768 | 0.753 | 0.766 | 0.751 | |
| | 2.5 | 0.562 | 0.569 | 0.549 | 0.554 | 0.537 | |
| | 5 | 0.436 | 0.442 | 0.426 | 0.433 | 0.422 | |
| Standard quality control point (µg/L) | OD450 | 0.497 | 0.498 | 0.472 | 0.494 | 0.473 | |
| | Antigen concentration (µg/L) | 3.56 | 3.64 | 3.86 | 3.54 | 3.71 | 3.5% |

The kit provided in Example 10 was tested in accordance with the one-step method provided in Example 20, and similar experimental results were also obtained. The kits of other examples were tested in accordance with the two-step or one-step method provided in Example 20, similar experimental results were obtained.

Example 23 Effects of Different GM Antigen Coating Solutions on Detection Reproducibility of Kit The kits prepared in Examples 4-9 were used to perform an inter-assay precision detection on the same sample to be tested according to the detection steps of Example 20. The same sample was tested once a day for 10 working days to study the effects of different GM antigen coating solutions on the detection reproducibility of the kit. The detection results are shown in Table 14 below.

TABLE 14

| | | Kit | | | | | |
|---|---|---|---|---|---|---|---|
| GM | Concentration ng/mL | Example 4 | Example 5 | Example 6 | Example 7 | Example 8 | Example 9 |
| | | OD450 | | | | | |
| Antigen standard | 0.25 | 1.223 | 1.272 | 1.245 | 1.241 | 1.223 | 1.205 |
| | 0.5 | 1.103 | 1.078 | 1.027 | 1.013 | 1.056 | 1.026 |
| | 1 | 0.894 | 0.931 | 0.907 | 0.89 | 0.909 | 0.916 |
| | 2.5 | 0.656 | 0.742 | 0.668 | 0.631 | 0.72 | 0.711 |
| | 5 | 0.446 | 0.521 | 0.441 | 0.442 | 0.514 | 0.513 |
| Sample to be tested | OD450 | 0.831 | 0.890 | 0.831 | 0.833 | 0.877 | 0.875 |
| | | 0.846 | 0.901 | 0.847 | 0.844 | 0.840 | 0.830 |
| | | 0.838 | 0.867 | 0.838 | 0.806 | 0.871 | 0.848 |
| | | 0.819 | 0.897 | 0.821 | 0.839 | 0.859 | 0.855 |
| | | 0.833 | 0.897 | 0.838 | 0.839 | 0.863 | 0.853 |
| | | 0.833 | 0.880 | 0.834 | 0.826 | 0.859 | 0.841 |
| | | 0.823 | 0.888 | 0.819 | 0.830 | 0.869 | 0.875 |
| | | 0.819 | 0.873 | 0.813 | 0.839 | 0.844 | 0.871 |

TABLE 14-continued

| GM | Concentration ng/mL | Kit | | | | | |
|---|---|---|---|---|---|---|---|
| | | Example 4 | Example 5 | Example 6 | Example 7 | Example 8 | Example 9 |
| | | OD450 | | | | | |
| Antigen concentration ng/mL | | 0.819 | 0.907 | 0.815 | 0.828 | 0.852 | 0.859 |
| | | 0.838 | 0.897 | 0.821 | 0.819 | 0.855 | 0.839 |
| | | 1.24 | 1.18 | 1.21 | 1.14 | 1.13 | 1.09 |
| | | 1.20 | 1.13 | 1.14 | 1.09 | 1.29 | 1.33 |
| | | 1.21 | 1.3 | 1.18 | 1.26 | 1.16 | 1.23 |
| | | 1.3 | 1.15 | 1.26 | 1.11 | 1.22 | 1.19 |
| | | 1.23 | 1.15 | 1.18 | 1.11 | 1.2 | 1.2 |
| | | 1.23 | 1.23 | 1.2 | 1.17 | 1.22 | 1.27 |
| | | 1.28 | 1.19 | 1.27 | 1.15 | 1.17 | 1.09 |
| | | 1.3 | 1.27 | 1.3 | 1.11 | 1.3 | 1.11 |
| | | 1.3 | 1.1 | 1.29 | 1.16 | 1.26 | 1.17 |
| | | 1.21 | 1.15 | 1.26 | 1.2 | 1.24 | 1.28 |
| CV % | | 3.27% | 5.37% | 4.40% | 4.45% | 4.57% | 6.95% |

As can be seen from the data in Table 14, the CV values of the results of the samples detected by each kit were less than 7%, indicating that each kit has a small dispersion degree of the detection results of the samples and good repeatability, and can be used for immunodetection of GM antigens; moreover, the CV value of the sample concentration detected by the kit prepared in Example 4 was the minimum, indicating that the coating solution in Example 4 is superior.

Example 24 Effects of Different Blocking Solutions on Detection Repeatability of Kit The kits prepared in Examples 10-11 were used to perform an inter-assay precision detection on the same sample to be tested according to the detection steps of Example 20. The same sample was tested once a day for 10 working days to study the effects of different blocking solutions on the detection repeatability of the kit. The detection results are shown in Table 15 below.

TABLE 15

| Kit | | Example 10 | Example 11 |
|---|---|---|---|
| GM | Concentration ng/mL | OD450 | |
| Antigen standard | 0.25 | 1.123 | 1.206 |
| | 0.5 | 0.974 | 1.053 |
| | 1 | 0.829 | 0.913 |
| | 2.5 | 0.626 | 0.689 |
| | 5 | 0.502 | 0.543 |
| Sample to be tested | OD450 | 0.762 | 0.861 |
| | | 0.758 | 0.849 |
| | | 0.773 | 0.851 |
| | | 0.756 | 0.846 |
| | | 0.759 | 0.839 |
| | | 0.762 | 0.825 |
| | | 0.771 | 0.833 |
| | | 0.753 | 0.819 |

TABLE 15-continued

| Kit | | Example 10 | Example 11 |
|---|---|---|---|
| GM | Concentration ng/mL | OD450 | |
| Antigen concentration ng/mL | | 0.773 | 0.861 |
| | | 0.758 | 0.849 |
| | | 1.38 | 1.23 |
| | | 1.41 | 1.3 |
| | | 1.31 | 1.29 |
| | | 1.42 | 1.32 |
| | | 1.4 | 1.36 |
| | | 1.38 | 1.45 |
| | | 1.32 | 1.4 |
| | | 1.44 | 1.49 |
| | | 1.31 | 1.23 |
| | | 1.41 | 1.3 |
| CV % | | 3.49% | 6.54% |

As can be seen from the data in Table 15, the CV values of the results of the samples detected by each kit were less than 7%, indicating that each kit has a small dispersion degree of the detection results of the samples and good repeatability, and can be used for immunodetection of GM antigens; moreover, the CV value of the sample concentration detected by the kit prepared in Example 10 was the minimum, indicating that the blocking solution in Example 10 is superior.

Example 25 Effects of Different Sample Treatment Solutions on Repeatability and Recovery Rate of Detection of Kit The kits prepared in Examples 12-18 were used to perform an inter-assay precision and recovery rate detection on the same sample to be tested (the concentration is known as 1.43 ng/mL) according to the detection steps of the two-step method in Example 20. The same sample was tested once a day for 10 working days to study the effects of different sample treatment solutions on the repeatability and recovery rate of detection of the kit. The detection results are shown in Table 16 below.

TABLE 16

| GM | Concentration ng/mL | Kit | | | | | | |
|---|---|---|---|---|---|---|---|---|
| | | Example 12 | Example 13 | Example 14 | Example 15 | Example 16 | Example 17 | Example 18 |
| | | | | | OD450 | | | |
| Antigen standard | 0.25 | 1.068 | 1.055 | 1.023 | 1.052 | 1.076 | 1.088 | 1.063 |
| | 0.5 | 0.894 | 0.909 | 0.871 | 0.896 | 0.913 | 0.929 | 0.912 |

TABLE 16-continued

| GM | Concentration ng/mL | Kit | | | | | | |
|---|---|---|---|---|---|---|---|---|
| | | Example 12 | Example 13 | Example 14 | Example 15 OD450 | Example 16 | Example 17 | Example 18 |
| | 1 | 0.745 | 0.743 | 0.713 | 0.740 | 0.728 | 0.764 | 0.756 |
| | 2.5 | 0.54 | 0.534 | 0.493 | 0.534 | 0.526 | 0.555 | 0.547 |
| | 5 | 0.405 | 0.406 | 0.374 | 0.378 | 0.389 | 0.412 | 0.419 |
| Sample to be tested | OD450 | 0.676 | 0.699 | 0.622 | 0.663 | 0.674 | 0.692 | 0.705 |
| | | 0.691 | 0.667 | 0.614 | 0.663 | 0.694 | 0.725 | 0.716 |
| | | 0.686 | 0.681 | 0.629 | 0.666 | 0.679 | 0.707 | 0.707 |
| | | 0.692 | 0.679 | 0.632 | 0.655 | 0.666 | 0.719 | 0.694 |
| | | 0.692 | 0.659 | 0.634 | 0.664 | 0.669 | 0.703 | 0.692 |
| | | 0.678 | 0.701 | 0.624 | 0.686 | 0.686 | 0.692 | 0.702 |
| | | 0.681 | 0.666 | 0.653 | 0.661 | 0.681 | 0.717 | 0.732 |
| | | 0.694 | 0.704 | 0.631 | 0.656 | 0.692 | 0.717 | 0.686 |
| | | 0.694 | 0.678 | 0.632 | 0.668 | 0.676 | 0.700 | 0.700 |
| | | 0.694 | 0.701 | 0.653 | 0.669 | 0.673 | 0.707 | 0.734 |
| | Antigen concentration ng/mL | 1.5 | 1.3 | 1.52 | 1.41 | 1.37 | 1.41 | 1.28 |
| | | 1.41 | 1.5 | 1.58 | 1.41 | 1.26 | 1.22 | 1.22 |
| | | 1.44 | 1.41 | 1.47 | 1.39 | 1.34 | 1.32 | 1.27 |
| | | 1.4 | 1.42 | 1.45 | 1.46 | 1.42 | 1.25 | 1.35 |
| | | 1.4 | 1.56 | 1.44 | 1.4 | 1.4 | 1.34 | 1.36 |
| | | 1.49 | 1.29 | 1.51 | 1.27 | 1.3 | 1.41 | 1.3 |
| | | 1.47 | 1.51 | 1.32 | 1.42 | 1.33 | 1.26 | 1.13 |
| | | 1.39 | 1.27 | 1.46 | 1.45 | 1.27 | 1.26 | 1.4 |
| | | 1.39 | 1.43 | 1.45 | 1.38 | 1.36 | 1.36 | 1.31 |
| | | 1.39 | 1.29 | 1.32 | 1.37 | 1.38 | 1.32 | 1.12 |
| | Mean value | 1.41 | 1.24 | 1.46 | 1.32 | 1.38 | 1.3 | 1.34 |
| | CV % | 3.23% | 7.65% | 6.34% | 4.38% | 3.78% | 5.49% | 7.18% |
| | Recovery rate | 100.93% | 98.48% | 102.91% | 97.32% | 93.71% | 92.19% | 88.46% |

As can be seen from the data in Table 16, the CV values of the results of the samples detected by each kit were less than 8%, indicating that each kit has a small dispersion degree of the detection results of the samples and good repeatability, and can be used for immunodetection of GM antigens; moreover, the CV value of the sample concentration detected by the kit prepared in Example 12 was the minimum, and the recovery rate was close to 100%, indicating that the treatment solution in Example 12 is superior.

Example 26 Comparison of Detection Results of Sample Between Kit of the Present Invention and Product of Bio-Rad Laboratories 24 samples were detected with the kit of the present invention (taking the kit provided in Example 12 of the present invention as an example) and the kit of Bio-Rad Laboratories (batch number: 6H0042), respectively. The specific results are shown in Table 17 below.

The determination criterion of the reference value of the kit of the present invention is that: the upper limit of the reference range is 0.85 μg/L, and the lower limit is 0.65 μg/L. If the sample has a concentration of ≥0.85 μg/L, it is determined to be positive; if the sample has a concentration of <0.65 μg/L, it is determined to be negative; and if the sample has a concentration between 0.65 ng/mL and 0.85 ng/mL, it is determined to be a suspected patient. The determination criterion of the kit of Bio-Rad Laboratories is that: if the sample has a I value of ≥0.5, it is positive, and if the sample has a I value of <0.5, it is negative.

TABLE 17

Comparative experiment results of the kit of the present invention and kit of Bio-Rad Laboratories

| | Kit of the present invention | | Kit of Bio-Rad Laboratories | | Actual results |
|---|---|---|---|---|---|
| | Concentration value | Positive and negative results | I value | Positive and negative results | Positive and negative results |
| 1 | 4.57 | + | 0.78 | + | + |
| 2 | 1.96 | + | 0.60 | + | + |
| 3 | 2.24 | + | 0.91 | + | + |
| 4 | 0.66 | ± | 0.46 | − | − |
| 5 | 1.33 | + | 0.97 | + | + |
| 6 | 0.58 | − | 0.41 | − | − |
| 7 | 0.81 | ± | 0.54 | + | + |
| 8 | 4.79 | + | 1.29 | + | + |
| 9 | 0.74 | ± | 0.40 | − | + |
| 10 | 1.27 | + | 1.37 | + | + |
| 11 | 0.69 | ± | 0.48 | − | − |
| 12 | 1.19 | + | 3.76 | + | + |
| 13 | 1.72 | + | 2.40 | + | + |
| 14 | 0.94 | + | 0.67 | + | + |
| 15 | 0.79 | ± | 1.33 | + | + |
| 16 | 1.27 | + | 1.79 | + | + |
| 17 | 0.58 | − | 0.46 | − | − |
| 18 | 0.78 | ± | 0.40 | − | + |
| 19 | 0.91 | + | 0.68 | + | + |
| 20 | 0.81 | ± | 0.61 | + | + |
| 21 | 0.57 | − | 0.40 | − | − |
| 22 | 1.05 | + | 0.64 | + | + |
| 23 | 1.20 | + | 1.51 | + | + |
| 24 | 0.66 | ± | 0.43 | − | − |

As can be seen from Table 17, 1) the kit of Bio-Rad Laboratories is a qualitative test product, which can only provide determination for positive and negative results and cannot provide a specific concentration; 2) when the antigen concentration of the detected sample is between 0.65 ng/mL and 0.85 ng/mL, the results detected by the kit of Bio-Rad Laboratories are highly variable, for example, for the ninth and eighteenth cases in Table 17, the actual results of which are positive, while both the results obtained by the kit of Bio-Rad Laboratories are negative, and the results obtained by the kit provided by the present invention are suspected patients, which need further determination. It can be seen that the kit provided by the present invention has more accurate and reliable detection result than the kit of Bio-Rad Laboratories.

The hybridoma cell under the accession number of CGMCC No. 13827 or the passage cell thereof provided by the present invention has stable performance, and the monoclonal antibody produced therefrom or the specific antigen-binding fragment thereof can specifically bind to the *Aspergillus* GM antigen. The detection kit prepared using the same has sensitivity and specificity of more than 95%, and very small inter-assay and intra-assay dispersion degrees, good repeatability and high stability; moreover, the detection kits prepared with different buffers of coating solutions, different GM antigen concentrations, different blocking solutions and different sample treatment solutions have small detection degree and good repeatability. The kit provided by the present invention can not only reduce the cost, but also can detect IA quickly and easily, has a detection limit of 0.85 ng/mL compared to 1 ng/mL of the existing product, which can detect IA earlier, and has more accurate and reliable detection results, so that the patient can be treated early, thereby improving the survival rate of the patient.

The above are only the preferred examples of the present invention, and are not intended to limit the present invention. Any modifications, equivalent substitutions, etc., made within the spirit and scope of the present invention, are intended to be included within the scope of the present invention.

The invention claimed is:

1. A hybridoma cell or a passage cell thereof having an accession number of CGMCC No. 13827.

2. A monoclonal antibody or a specific antigen-binding fragment thereof, wherein the monoclonal antibody is produced by the hybridoma cell of claim 1, and the specific antigen-binding fragment is capable of specifically binding to *Aspergillus* galactomannan antigen.

3. The monoclonal antibody or specific antigen-binding fragment thereof of claim 2, wherein the specific antigen-binding fragment is selected from the group consisting of (Fab')2, Fab, Fv, scFv, diabody, linear antibody or multispecific antibody.

4. A detection kit comprising the monoclonal antibody or specific antigen-binding fragment thereof of claim 2.

5. The detection kit of claim 4, wherein the specific antigen-binding fragment is selected from the group consisting of $(Fab')_2$, Fab, Fv, scFv, diabody, linear antibody or multispecific antibody.

6. The kit of claim 4, further comprising one or more of a buffer of a coating solution, a blocking solution, and a sample treatment solution.

7. The kit of claim 6, wherein the buffer of the coating solution is selected from the group consisting of 0.1 mol/L Tris-HCl, 0.1 mol/L PBS, 0.05 mol/L CBS, 0.1 mol/L CBS, 0.2 mol/L CBS, and normal saline; the blocking solution is selected from the group consisting of 2% newborn calf serum, 5% newborn calf serum and 8% newborn calf serum; and the sample treatment solution is selected from the group consisting of 0.03 mol/L EDTA, 0.1 mol/L EDTA, 0.12 mol/L EDTA, 0.05 mol/L proteinase K, 0.1 mol/L proteinase K, 0.2 mol/L proteinase K, 5% DMSO, 15% DMSO and 30% DMSO.

8. The kit of claim 6, wherein the sample treatment solution is 0.12 mol/L EDTA.

9. The kit of claim 6, wherein the buffer of the coating solution is 0.1 mol/L Tris-HCl with a pH of 6.0-9.0.

10. The kit of claim 6, wherein the blocking solution is 8% newborn calf serum.

11. The kit of claim 4, further comprising a galactomannan antigen-coated solid phase carrier and a galactomannan antigen standard.

12. The kit of claim 4, wherein the monoclonal antibody is an enzyme-labeled monoclonal antibody.

13. The kit of claim 4, wherein the monoclonal antibody is a monoclonal antibody not labeled with an enzyme, and the kit further comprises an enzyme-labeled secondary antibody, and the enzyme-labeled secondary antibody can bind to the monoclonal antibody.

14. A preparation method of the monoclonal antibody or specific antigen-binding fragment thereof of claim 2, including a step of culturing a hybridoma cell or passage cell thereof having an accession number of CGMCC No. 13827.

15. The preparation method of claim 14, wherein the specific antigen-binding fragment is selected from the group consisting of $(Fab')_2$, Fab, Fv, scFv, diabody, linear antibody or multispecific antibody.

16. A method for detecting *Aspergillus* infection, comprising a step of detecting GM antigen with the monoclonal antibody or specific antigen-binding fragment thereof of claim 2 by competitive ELISA.

17. The method of claim 16, wherein the specific antigen-binding fragment is selected from the group consisting of $(Fab')_2$, Fab, Fv, scFv, diabody, linear antibody or multispecific antibody.

* * * * *